(12) United States Patent
Krans et al.

(10) Patent No.: US 9,392,963 B2
(45) Date of Patent: Jul. 19, 2016

(54) BREATH PACING SYSTEM AND METHOD FOR PACING THE RESPIRATORY ACTIVITY OF A SUBJECT

(75) Inventors: Jan Martijn Krans, Den Bosch (NL); Bartel Van De Sluis, Eindhoven (NL); Juergen Vogt, Eindhoven (NL); Ronaldus Aarts, Geldrop (NL); Tim Tijs, Helmond (NL); Ype Brada, Leeuwarden (NL); Maarten Van Den Boogaard, Westerbroek (NL); Jan Bennik, Urk (NL); Roy Raymann, Waalre (NL); Petronella Zwartkruis-Pelgrim, Nuenen (NL); Jia Du, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 83 days.

(21) Appl. No.: 13/884,010

(22) PCT Filed: Nov. 15, 2011

(86) PCT No.: PCT/IB2011/055093
§ 371 (c)(1),
(2), (4) Date: May 8, 2013

(87) PCT Pub. No.: WO2012/069959
PCT Pub. Date: May 31, 2012

(65) Prior Publication Data
US 2013/0231522 A1    Sep. 5, 2013

(30) Foreign Application Priority Data

Nov. 23, 2010  (EP) .................................. 10192288

(51) Int. Cl.
*A61M 21/00* (2006.01)
*A61B 5/08* (2006.01)
*A61B 5/00* (2006.01)

(52) U.S. Cl.
CPC ................ *A61B 5/0816* (2013.01); *A61B 5/08* (2013.01); *A61B 5/486* (2013.01)

(58) Field of Classification Search
CPC .......... A61B 5/08; A61B 5/0816; A61B 5/486
USPC ................................ 600/26–28; 128/897–899
See application file for complete search history.

(56) References Cited

U.S. PATENT DOCUMENTS 6,062,216 A * 5/2000 Corn ........................ 128/204.23
7,691,049 B2   4/2010 Wood et al.
(Continued)

FOREIGN PATENT DOCUMENTS

CN    101035584 A    9/2007
CN    101528294 A    9/2009
(Continued)

OTHER PUBLICATIONS

Kapitza et al: "First Non-Contingent Respiratory Biofeedback Placebo Versus Contingent Biofeedback in Patients With Chronic Low Back Pain: A Randomized, Controlled, Double-Blind Trial"; Applied Psychophysiology and Biofeedback (2010), vol. 35, No. 3, Sep. 2010, pp. 207-217.

(Continued)

*Primary Examiner* — Navin Natnithithadha
*Assistant Examiner* — Sunita Reddy

(57) ABSTRACT

To provide a breath pacing system and a corresponding method for pacing the respiratory activity of a subject that provide the possibility to adapt the output signal to the respiration characteristics of the subject automatically and effectively a breath pacing system (10) for pacing the respiratory activity of a subject and a respective method is proposed, comprising: an input unit (14) for generating or determining an input signal related to a respiration characteristic of a subject, a signal analyzing unit (16) provided to recognize a signal pattern within the input signal, and an output unit (12) for outputting output signals corresponding to a desired breathing sequence, wherein said output unit (12) is provided to be activated, upon a starting signal, to output a sequence of output signals comprising a signal pattern related to a previously recognized signal pattern.

19 Claims, 3 Drawing Sheets

(56) References Cited

U.S. PATENT DOCUMENTS

| | | | |
|---|---|---|---|
| 2003/0212303 A1* | 11/2003 | Kahn | A61B 5/0806 600/3 |
| 2006/0047202 A1 | 3/2006 | Elliott | |
| 2006/0102171 A1* | 5/2006 | Gavish | A61B 5/0816 128/95.1 |
| 2007/0114206 A1 | 5/2007 | Mitrovic et al. | |
| 2007/0203433 A1* | 8/2007 | Murphy | A61H 7/001 601/15 |
| 2009/0114216 A1 | 5/2009 | Hung et al. | |
| 2009/0192402 A1 | 7/2009 | Corn | |
| 2010/0152545 A1* | 6/2010 | Ramsay | A61B 5/0002 600/301 |
| 2010/0240945 A1* | 9/2010 | Bikko | G10L 21/00 600/28 |

FOREIGN PATENT DOCUMENTS

| | | |
|---|---|---|
| EP | 2277437 A1 | 1/2011 |
| JP | 2002301047 A | 10/2002 |
| WO | WO2010018485 A1 | 2/2010 |

OTHER PUBLICATIONS

Dijk et al: "Breathe With the Ocean: A System for Relaxation Using Audio, Haptic and Visual Stimuli"; Philips Research, Eindhoven, The Netherlands, pp. 48-60, 2010.

* cited by examiner

BREATH PACING SYSTEM AND METHOD FOR PACING THE RESPIRATORY ACTIVITY OF A SUBJECT

FIELD OF THE INVENTION

The invention relates to the field of pacing the respiratory activity of a subject, especially to a breath pacing system and a corresponding method for pacing the respiratory activity of a subject.

BACKGROUND OF THE INVENTION

A slow and regular breathing activity is considered to be beneficial for relaxation. To support the breathing process, several different breath pacing devices are known to provide output signals that correspond to a desired regular breathing rhythm and can easily be perceived by a user.

US-20070114206 discloses a breath pacing device comprising respiration sensors for producing a breath condition signal that is displayed to a user as a feedback to his actual respiration. On the reception of this signal, the user can adapt his respiration practice for learning purposes. In this case the sensors are integrated into an article of clothing like a shirt, for example. This system is not suitable where relaxation is desired.

A pacing signal can also be, for example, a light that changes its intensity, color or shape periodically according to the desired respiration cycles. In one possible application, breath pacers can be used in bed by a person to reduce sleep onset latency. These breath pacers project a light spot of slowly varying size on the ceiling of the bedroom. A further example for a pacing signal is an audio or video signal.

One problem related to the operation and control of such devices lies in the necessity to find a suitable operation mode at the beginning of a pacing sequence or, in other words, a "starting point" at which the system begins to operate. The system works most efficient when the output signal is adapted to the present respiration characteristics of the user. This stands especially for the respiration rate, i.e., the frequency of the respiration cycle, and other time characteristics within each respiration cycle (e.g. inhalation time, exhalation time, pause times) but also for the amplitude. An output signal synchronized to the present user's breathing frequency helps the user to adapt to the pacing rhythm of the apparatus. However, at present there is no efficient and practical way to adapt the output signal to the user's respiration rate automatically.

SUMMARY OF THE INVENTION

It is therefore an object of the present invention to provide a breath pacing system and a corresponding method for pacing the respiratory activity of a subject that provide the possibility to adapt the output signal to the respiration characteristics of the subject automatically and effectively.

This object is achieved by a breath pacing system according to claim 1, as well as by a corresponding method according to claim 15.

In the breath pacing system according to the present invention, an input unit is used to generate or to determine an input signal that is related to the respiration activity of the user. Such an input unit can be represented by a sensor that monitors the respiration activity directly or by a user interface to receive signals that correspond to the respiration. The input signal is analyzed by a signal analyzing unit with regard to a signal pattern comprised within the input signal. Upon a starting signal, the output unit is activated to output a sequence of output signals that comprise a signal pattern related to a signal pattern that has been previously recognized.

When the breath pacing system is used, the output unit may first be inactive so that it does not generate output signals. Only the input unit, like a suitable sensor, is active to generate input signals corresponding to the respiration activity of the user. According to this activity, the input signal is generated and analyzed. In the moment when the starting signal is generated, the output unit is switched automatically into its active mode and begins to output a sequence of output signals that have a structure related to one that has already been recognized. Thus it is possible to synchronize the output signals with the "breathing rhythm" represented by the input signal. An important characteristic of the signal pattern is, for example, the actuation frequency or amplitude or the inhale to exhale ratio that can be adapted to the present breathing rhythm when beginning to output an output signal. However, other characteristics can be acknowledged in this context.

There are several ways to generate the starting signal, depending on an active input by the subject, for example, by means of a user interface that is also used as the above mentioned input unit to generate the input signal itself or an additional user interface, or on the recognition of a signal pattern in a monitoring process or in a previous operation period, as will be explained in more detail in the following.

It is noted that the signal pattern of the output signal does not necessarily have to be constantly adapted to the signal pattern recognized within the input signal. It is rather sufficient to adapt the signal pattern at the beginning of the sequence of output signals and to change the signal pattern of the output signals during a sequence according to a predetermined pattern to correspond to a desired breathing sequence. In other words, the adaption of the structure of the output signal may only take place at the beginning of the sequence, while the output signal may be independent from the present respiration activity of the subject in the further course of the sequence.

According to a preferred embodiment of the present invention, the output unit is provided as a tactile output unit for outputting tactile output signals. This embodiment provides the advantage that the generated output signals are haptically perceivable, and the system works even in a dark environment and can be used without disturbing other persons.

According to another preferred embodiment of the present invention, the input unit is integrated into the output unit. This leads to a compact and user-friendly design of the whole apparatus. However, the input unit may be arranged externally to the output unit and may be also placed outside a device comprising the output unit. In case of an external input unit, the signal derived from the input unit is communicated to the signal analyzing unit.

According to a preferred embodiment, the input unit is represented by a user interface for receiving a user input for adjusting a characteristic of the sequence of output signals. In this case the user can input a signal that directly represents his present respiration characteristic, for example, by executing a periodic movement (e.g. pressing and releasing) that mimics his present (or a desired) respiration activity, or he directly presets certain characteristics of the output signals. Such characteristics can be related to, inter alia, the identity of the subject, her/his age, gender, or physiological conditions, etc.

According to possible embodiments of the present invention, the input unit is represented by; inter alia, a mouse wheel, a keyboard, at least one button, a touch screen or a touch pad. For example, a signal characteristic can be adjusted by scrolling the wheel. Pressing the wheel may have another function, for example, generating the starting signal to output a sequence of output signals. The input unit can also be used to turn off the apparatus.

According to another embodiment, a squeeze sensor or pressure switch can be triggered by the user at the start of inhalation and/or exhalation, to align with the user's own respiration rate and/or inhalation and exhalation times.

According to another embodiment, the input signal is provided to be generated by a sensor for sensing a characteristic of the subject. By such a sensor the respiration activity of the subject can directly be monitored without any necessity of an input by the user.

It is noted that the above mentioned embodiments of the input unit as a user interface and a sensor do not necessarily exclude each other, i.e. it is possible to combine both functions in one input unit. Thus it is possible to produce an output signal that is based partially on a user input and to another part on a measurement of the respiration behavior of the subject. For example, one characteristic of the output signals can be pre-set by the user, while this (or another) characteristic is modified in the further progress of the sequence on the basis of the measurement results obtained by means of the sensor.

Preferably the starting signal is provided to be generated upon the recognition of a respiration signal pattern gained within at least one monitoring phase for monitoring the respiration activity of the subject. Such a monitoring phase can be, for example, a calibration phase preceding the activation of the output unit. In this calibration phase, the subject's respiration activity is monitored to derive a pattern from it. When a pattern has been identified, the output unit can begin to generate output signals with a corresponding pattern, e.g. with a frequency synchronized to the monitored frequency or having a certain relation to it. Another example for a monitoring phase is a foregoing operation period of the system wherein respiration data are acquired. These data can also be used to choose a desired starting frequency for the pacing process.

According to another preferred embodiment, the length of the monitoring phase is controlled depending on the progress of the respiration activity of the subject within the monitoring phase. For example, the length of a calibration phase can depend on the slope of the monitored respiration activity.

According to still another embodiment of the present invention, the sequence of output signals starts with a signal pattern related to a signal pattern gained within a previous monitoring phase.

Preferably the sequence of output signals starts with a frequency, an inhale to exhale ratio and/or amplitude related to a frequency, or an inhale to exhale ratio and/or amplitude contained in a signal pattern acquired from a previous monitoring phase. For example, a certain inhale to exhale ratio is contained in a signal pattern of a previous monitoring phase, and the sequence of output signals starts with an inhale to exhale ratio that stands in a distinct relation to it.

More preferably the further progress of the sequence of output signals is determined on the basis of signal patterns gained within previous monitoring phases.

According to another embodiment, the sequence of output signals comprises a slow down phase in which the frequency of the output signal is decreased.

More preferably the amplitude of the output signal is increased in the slow down phase. It is further possible to decrease its frequency at the same time.

According to still another embodiment of the present invention, the sequence of output signals comprises a fade out phase in which the amplitude of the output signal is decreased. During this phase the pacing frequency can be maintained.

The invention is further related to a method for pacing the respiratory activity of a subject, comprising: generating or determining an input signal related to a respiration characteristic of a subject; analyzing the input signal to recognize a signal pattern, and upon a starting signal, initiating an output of a sequence of output signals comprising a signal pattern related to a previously recognized signal pattern.

BRIEF DESCRIPTION OF THE DRAWINGS

These and other aspects of the invention will be apparent from and elucidated with reference to the embodiments described hereinafter. In the drawings.

DETAILED DESCRIPTION OF EMBODIMENTS

Figure 1:
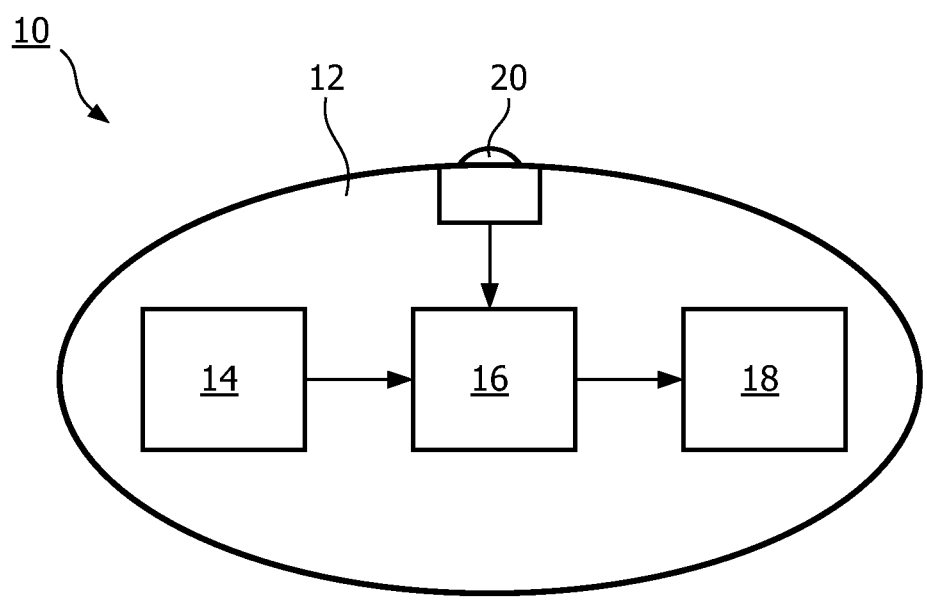
FIG. 1 is a schematic cross section through one embodiment of a breath pacing system according to the present invention.

The breath pacing system in FIG. 1 is provided as a tactile breath pacing system 10 comprising a tactile output unit 12 that determines the outer shape and appearance of the pacing system 10. As will be further described, all functional components of the tactile breath pacing system 10 are integrated into this tactile output unit 12. A tactile breath pacing system 10 is only one example of a breath pacing system according to the present invention, and its tactile output unit 12 may be replaced by any other suitable output unit for generating output signals that can be perceived by a subject, for example, by an acoustic output unit or a visual output unit. The following description will refer to a tactile breath pacing system 10 without limiting the scope of the present invention in this respect.

In the present example, the tactile output unit 12 may be a cushion, pillow, pad, stuffed toy, mobile phone, wristband or watch, although it can have different kinds of shapes and sizes. These examples are not understood as limiting but the tactile output unit can have any other suitable size or shape. The respective output unit 12, like a cushion or pad, is provided to change its size periodically, especially its thickness, and this change is a tactile output signal perceivable by a subject that is in close contact with the tactile output unit 12. The tactile output signals outputted by the tactile output unit 12 serve to pace the respiratory activity of the subject. In case of a mobile terminal or watch, a vibrating function could be used.

A sensor 14 as an input unit may be integrated into the tactile output unit 12 to determine a respiration characteristic, especially the respiration rate of the subject. In the present embodiment, the sensor 14 may be e.g. an airflow sensor represented by a microphone. Blowing against the microphone is interpreted as an exhale activity of the subject, while the time intervals between two blowing intervals are interpreted as inhale phases. To measure this airflow, the sensor is placed directly at the surface of the tactile output unit 12. In case an airflow sensor is used to detect air flow during exhalation (for instance when blowing) and/or inhalation), this air flow sensor preferably comprises a temperature sensing element, for example, a thermistor whose resistance varies with temperature. Under technical aspects, the airflow sensor does not necessarily have to be a microphone but can also be represented by other types of sensors, for example, by an anemometer or a temperature sensing element like a thermistor. Temperature differences in inhaled and exhaled air can be interpreted to identify the inhale and exhale phases of the respiration activity. Moreover, one option is to use the sensor to analyze the chemical composition of the exhaled air and to measure the percentage of $CO_2$ contained therein. This information can further be used to determine the character of the breathing activity and to adapt the pacing characteristics thereto.

Alternatively, the airflow sensor used in this embodiment as the sensor 14 could be replaced by a body motion sensor to monitor the respiratory activity of the subject. This embodiment is based on the idea that the respiratory activity leads to periodic movements of the subject's body that can easily be measured by a body motion sensor. An accelerometer is one example for such a body motion sensor to determine the respiration rate from chest or abdomen movements. Compared to an airflow sensor, it provides the advantage that it can be completely integrated into the tactile output unit 12 without being accessible from the outside. When there is no movement measured for a certain amount of time, this state can be interpreted as a situation where there is no contact of the subject with the tactile output unit 12, and the tactile breath pacing system 10 can automatically be turned off. This is also possible in the embodiment using the airflow sensor, interpreting a lack of input, i.e. no air flow to be measured for a certain amount of time by the airflow sensor as a situation in which the tactile breath pacing system 10 is not used.

The body motion sensor can also comprise a motion detector in the form of a drop of current conducting material that can move between a position where it facilitates a current flowing between electrodes and a position where no current can flow, such that the current is modulated by the movement of the drop. As described above, such a mechanism can be used to shut down the tactile pacing system 10 or setting it into a standby mode when no modulation takes place.

Another embodiment of the sensor 14 is a photopletysmograph (PPG) to analyze a respiratory pattern from a blood volume pulse signal. In one common embodiment, the skin of the subject (for example, on a finger or wrist) is illuminated and the change of light absorption due to the respiratory activity as measured. The user can operate the photopletysmograph by placing her/his finger on top of a window present at the surface of the tactile output unit 12.

Alternatively and/or additionally an externally arranged radar sensor could be used for measuring a body's motion to derive the input signal related to the respiration signal. Another embodiment of such a remote body sensor is a weight or pressure sensor for detecting a mechanical pressure applied by the subject, corresponding to her/his respiration activity. Such a sensor may comprise a pressure sensitive foil.

It is also possible to use a camera as a sensor for this purpose.

Further operation units of the tactile breath pacing system 10 are a signal analyzing unit 16 and an actuator 18, both being integrated into the tactile output unit 12. The signal analyzing unit 16 receives an input signal from the sensor 14 indicative of the respiration rate of the subject. The sensor 14 generates this respiration signal according to the measured respiration rate. The signal analyzing unit 16 is provided to analyze the input signal and to search for signal patterns contained within the input signal. Moreover, the signal analyzing unit 16 is provided to control the actuator 18 according to the result of this analysis, as will be described in the following. The actuator 18 is provided to induce a movement of the tactile output unit 12 to output the tactile output signals. That is, according to the movement of the actuator 18, the tactile output unit 12 moves, and this motion is perceivable by the subject. For example, the tactile output unit 12 can increase or decrease its size or can change its outer shape. However, other haptically or tactile perceivable changes of the outer or inner appearance of the tactile output unit 12 can be taken into account. The tactile output unit 12 can also perform haptically perceivable clicks or other force actions to give a perceivable signal to the user, for instance due to rotating motor which might give additional pacer cue information.

The tactile breath pacing system 10 may further comprise a rechargeable power supply (not shown) like a rechargeable battery or an accumulator. This enables a wireless operation of the pacing device without any disturbing connections to a mains supply, further improving its user friendliness.

The tactile output unit 12 is activated to output a sequence of tactile output signals when an input signal is generated. In the present embodiment, this starting signal is generated by the signal analyzing unit 16 when a signal pattern has been recognized within the input signal as being a respiration signal. This means that at least one respiration characteristic, for example, the respiration rate, has been identified as the input signal. If this is the case, the signal analyzing unit 16 controls the actuator 18 to initiate a sequence of tactile output signals that comprises a signal pattern that is related to the signal pattern that has been recognized. For example, these tactile output signals have the same or a similar frequency or amplitude as the measured respiration signals. Another possibility is that the signal pattern of the generated tactile output signals has a certain relation to the recognized signal pattern. Just to give one example, the frequency of the tactile output signals may be somewhat lower than the measured respiration rate. Also, the ratio between expand and contract time of the actuator maybe somewhat different than the inhale to exhale ratio measured by the respiration sensor. The signal analyzing unit 16 may comprise a computer program to control the actuator 18 accordingly.

By generating a sequence of tactile output signals with a signal pattern that is related to the recognized signal pattern, it is possible to synchronize the generated tactile output signals to the present respiration behavior of the user. In the present embodiment the tactile output unit 12 does not generate tactile output signals until a signal pattern has been recognized within the input signal by the signal analyzing unit 16. Once a pattern has been recognized, the starting signal is generated for the tactile output unit 12 to begin with the output of the sequence of tactile output signals. It is also possible to begin with the generation of tactile output signals without being influenced by a measurement taken during an initial monitoring phase and to start the output of the sequence of tactile output signals according to a recognized signal pattern from an earlier monitoring phase stored within the system, upon the starting signal.

As an additional input unit, a mouse wheel 20 is provided at the surface of the tactile output unit 12. The mouse wheel 20 is integrated into the tactile output unit 12 so that it is accessible from the outside. It represents a user interface to adjust a characteristic of the sequence of tactile output signals. For example, the user can choose and/or adjust a respiration frequency or amplitude as an input signal for the signal analyzing unit 16. One further function of the mouse wheel 20 could be to generate a starting signal for initiating the output of tactile output signals when it is pressed by the user. For example, when the user has finished the adjusting procedure, she/he presses the mouse wheel 20 to start the pacing. In the same way the user may stop the output of tactile output signals by pressing the mouse wheel 20 another time.

A mouse wheel 20 is only one possible embodiment of a user interface and can be replaced by a keyboard, one or more buttons or switches, a touch screen, a touch pad, a squeeze sensor or pressure switch or the like. Moreover, the user interface can be provided to output a status information about the tactile breath pacing system. The status information can be generated by a visual display or an audio signal of any desired type, e.g. indicating lights, a sound signal, or a haptic signal like a buzzer. Moreover, a speaker or a display integrated into or connected to the tactile output unit 12 can be used to output instructions to the user on how to use the device.

It is noted that the mouse wheel 20 may represent one alternative to the provision of a sensor, that is, a user interface can replace a sensor as an input unit to generate the input signal for the signal analyzing unit 16. However, it is also possible to combine both functions of a user interface and a sensor in one input unit or to provide different input units, each generating input signals for the signal analyzing unit 16. Thus a tactile output signal can be generated that is based partially on a user input via the user interface and to another part on a measurement of the respiration behavior of the subject. For example, at least one characteristic of the tactile output signals can be set by the user according to his identity and/or other personal conditions, like his age. This characteristic can be used to set the conditions of the tactile output signals at the start of the pacing process. Measurement results obtained by means of the sensor can be used during the pacing process to adjust and to modify the sequence of tactile output signals. The signal analyzing unit 16 can also use previously stored parameters, characteristics or algorithms to calculate the tactile output signals.

Figure 2:
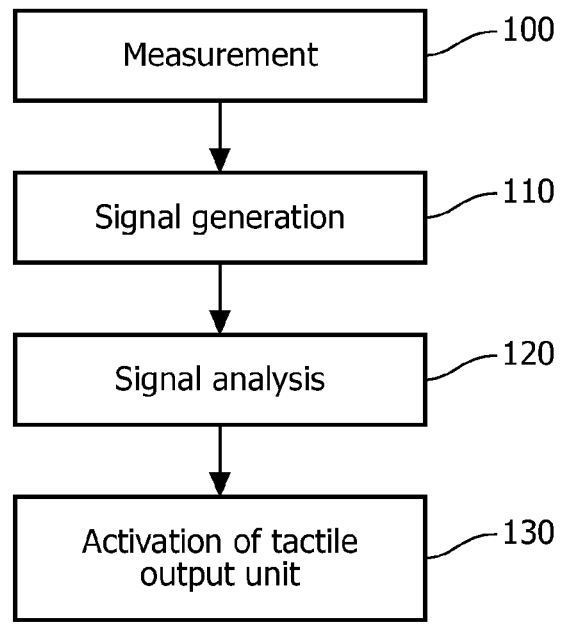
FIG. 2 is a flow diagram showing schematically one embodiment of the inventive method for pacing the respiratory activity of a subject.

The flow diagram in FIG. 2 shows one scenario for a process for generating a pacing signal. In the following description it is supposed that the input signal is generated by the sensor 14 only. The respiration activity of the subject is measured (step 100) by the sensor 14 (as shown in FIG. 1) to generate an input signal indicative of a respiration characteristic of the subject (such as respiration rate) (step 110). This input signal represents the periodic respiration activity including inhale and exhale phases. The input signal is then transmitted to the signal analyzing unit 16 to be analyzed (step 120). In this analysis, the signal analyzing unit 16 looks for signal patterns within the input signal. Once a pattern has been recognized, the starting signal is generated for the actuator 18, and the tactile output unit 12 is activated (step 130) to begin with the output of a sequence of tactile output signals. At least at the beginning of this sequence, the tactile output signals comprise a signal pattern corresponding to the recognized signal pattern of the input signal analyzed by the signal analyzing unit 16 in step 120.

One possibility is to take the inhale to exhale ratio as a reference for generating the tactile output signals. Observations have shown that an inhale to exhale ratio smaller than 1 is beneficial for relaxation. In the case where a present inhale to exhale ratio of the subject is identified, for example, to be larger than 1 or equal to 1, the tactile output unit 12 may output a sequence of tactile output signals starting with an expand time corresponding to the present inhale time of the subject, which is found to be natural by most persons, but with a contract time larger than the exhale time. Consequently the pacer rate starts with a frequency lower than the measured respiration frequency. It should be noted that a contraction of the tactile output unit 12 may not necessarily be linked to the exhale phase (and consequently, an expansion of the device be linked to the inhale phase), but the roles of the contraction and the expansion can also be reversed.

As already mentioned, the input signal may be generated not by a sensor 14 but can also originate from a user interface as an input unit for adjusting a characteristic of the sequence of tactile output signals. For example, the user adjusts a personal respiration characteristic (frequency, amplitude or the like) by means of the mouse wheel 20, related to her/his identity and personal condition. This can be interpreted as an input signal by the signal analyzing unit 16 in step 120 in FIG. 2, and according to the result of this analysis, the tactile output unit 12 begins to output of a sequence of tactile output signals.

As an alternative, input signals of the sensor 14 as well as of the user interface, i.e. the mouse wheel 20 can be taken into account. For example, the user may input personal respiration characteristics as described above to determine preconditions for the pacing process. The sensor 14 may then monitor the present respiration activity of the subject, and the signal analyzing unit 16 will calculate a sequence of tactile output signals on the basis of both kinds of input signals.

To provide guidance for the breathing activity, it is preferred to control the length and frequency of the phases (see FIG. 3) within the sequence of tactile output signals based on the calibration data obtained, (or calibration data obtained during a previous session), so that a relaxing effect takes place. The signal analyzing unit 16 can determine the further progress of the sequence, beginning with the frequency corresponding to the recognized respiration frequency and changing it in the further course of the tactile output signal.

Figure 3:
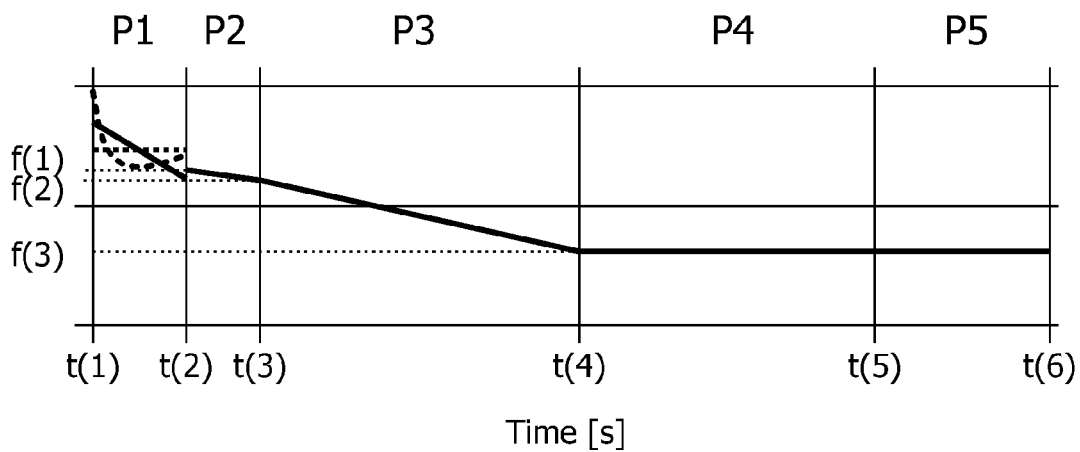
FIGS. 3 and 4 are diagrams demonstrating the development of the pacing rate over time according to one embodiment of the present invention.

The diagram in FIG. 3 shows one possible pacing scenario with respect to the chronological development of the pacing rate (frequency) of the tactile output signal. The horizontal axis of the diagram in FIG. 3 represents the time, while the vertical axis represents the pacing rate. The time axis is divided into five different phases, the first phase beginning at t(1)=0 being a calibration phase (P1), in which the tactile output unit 12 is passive and does not output tactile output signals. The calibration phase (P1) is followed by phases (P2), (P3), (P4) and (P5) in which the tactile output unit 12 is active and outputs a sequence of tactile output signals. This activity period starts with a starting phase (P2) and is followed by a slow down phase (P3), a phase of constant pacing rate (P4) and a fade out phase (P5).

In the calibration phase (P1), the respiration activity of the subject is monitored by the sensor 14 that generates an input signal. This input signal is analyzed by the signal analyzing unit 16. By this monitoring activity the progress of the respiration of the subject can be analyzed, resulting in a curve that shows the respiration activity. In FIG. 3, different curves are shown as three examples of developments of the respiration rate during the calibration phase.

Each curve represents a "respiration rate profile" of the subject. From this profile the signal analyzing unit 16 can derive a starting point of the pacing activity, that is, a suitable pacing rate at the beginning of the sequence of tactile output signals. The pacing rate (frequency) is only one possible characteristic of the tactile output signal that can be chosen. Another characteristic could be the pacing amplitude that is also derived from the results of the measurements of the calibration phase (P1). Generally speaking, the signal analyzing unit 16 tries to find a signal pattern within the respiration profile represented by the input signal, and when such a pattern is recognized, a starting signal is generated for the actuator 18 to output a tactile output signal that relates to this signal pattern.

It is also possible to acknowledge results of previous monitoring phases in the search of the signal pattern within the input signal. This means that the calibration phase (P1) shown in FIG. 3 is only one example of such a monitoring phase, in which the tactile output unit is passive. However, such a monitoring phase can also be represented by a previous operation period of the tactile breath pacing system 10 in which the respiration activity of the subject has been monitored. It is also noted that a calibration phase (P1) preceding the output of a sequence of tactile output signals may not always be necessary. The starting point of the pacing activity can rather be chosen merely on the basis of history data, i.e. previous operation periods, as described above.

When the signal pattern has been recognized and the input signal has been generated, the pacing begins at a starting level f(1) of the pacing rate at the time t(2) at the beginning of the starting phase (P2). During this phase (P2) the pacing rate of the tactile output signal slightly decreases in the present embodiment in FIG. 3. The progress of this decrease, i.e. the slope of the curve representing the pacing rate over time can also depend on the calibration results. It is also possible to keep the pacing rate constant during this phase (P2). The starting phase (P2) is followed by a slow down phase (P3) with a stronger decrease of the pacing rate until time t(4). During the slow down phase (P3) the pacing rate decreases from the value f(2) to f(3). This value f(3) corresponds to a target respiration rate of a desired breathing sequence and can be derived from respiratory characteristics measured during the calibration phase. According to one example, the pacing rate f(3) may correspond to a value of 60% of the measured respiration rate at the start.

The slow down phase (P3) is followed by a phase of constant pacing rate (4) in which the pacing rate stays constant on the level f(3). The length of the phase (P4) may be calculated on the basis of previous monitoring periods, i.e. previous operation phases of the tactile breath pacing system 10 and (optionally) the calibration phase (P1). In the slow down phase (P3), the pacing amplitude (not shown) can increase linearly to a certain level and can stay on this level during the phase (P4). Other characteristics of the tactile output signal can also be changed in a predetermined manner during the phases (P2) to (P5).

The phase (P4) is followed by a fade out phase (P5) with a constant pacing rate on the level f(3). In phase (P5), the pacing amplitude may decrease to zero, so that a pacing activity ends at the time t(6) in this example.

While the length of the phases (P4) and (P5) can be determined on the basis of monitoring results, as described above, their length can also be determined on the basis whether there is an input into the sensor 14. When the sensor does not generate an input signal, i.e. the periodic signal indicative of the respiration rate of the subject, this can be taken as a sign that there is no contact between the subject and the tactile output unit 12, and the tactile breath pacing system 10 is not used. It is then possible to start the fade out phase (P5) or the finish the pacing process completely.

The pacing process can be stopped when it has been determined that the subject has fallen asleep or has relaxed to a desired extent. The fade out phase (P5) can be started when a certain characteristic or signal pattern has been recognized within the input signal, or the system is shut down immediately in this case. For example, the sensor 14 may measure a respiration frequency, amplitude or inhale to exhale ratio signaling a weak breathing activity that indicates a sleeping or deeply relaxed state of the subject. A corresponding signal pattern of the input signal originating from the sensor 14 will be recognized by the signal analyzing unit 16, and it will generate a stopping signal for the tactile output unit 12 to stop the sequence of tactile output signals immediately or to start the fade out phase (P5) in which the pacing amplitude decreases to zero, and the whole system turns off. In this embodiment the signal analyzing unit 16 is provided to control the length of the sequence of tactile output signals based on characteristics of the input signal that may correspond to a certain condition of the subject.

What has been described before is only one possible pacing scenario. Another possibility is to dispense the calibration phase (P1) and to derive the respiration rate profile only from previous operation periods of the tactile breath pacing system 10. This means that prior periods of use are taken as monitoring periods in which a signal pattern can be detected.

A third scenario is to acknowledge not only an input signal generated by a sensor 14 but also originating from a user interface like the mouse wheel 20 in FIG. 1. For example, the user may adjust or choose personal respiration characteristics as described above to determine preconditions for the pacing process and input them into the user interface. Such a personal characteristic may refer to the user's identity, the age, gender or another personal feature. This input can then be used as an input signal for choosing a pacing characteristic at the beginning of the sequence of tactile output signals as a "starting point". In the further pacing progress during the phases (P2) to (P5) in FIG. 3, the sequence of tactile output signals can be tuned, i.e. further adapted on the basis of sensor signals that have been collected in a calibration phase or in a phase of prior use as history data.

In all these scenarios it is possible to generate a stopping signal to stop the tactile output unit 12 from further producing tactile output signals. The stopping signal can be generated by the signal analyzing unit 16 upon the recognition of a certain signal pattern contained within the input signal originating from a sensor 14, as described above. However, other factors can be taken into account, for example, the running time of the sequence so that the stopping signal cannot be generated until a predetermined time period has passed. It is also possible to generate the stopping signal only on a time basis, i.e. to determine a fixed time period as the duration of the sequence or to determine it dependent on a user's input via the user interface. In this embodiment the signal analyzing unit 16 is provided to control the length of the sequence of tactile output signals based on a time schedule that may be programmed and/or can be changed by the user.

In this version it is possible to influence the output signal by an input unit that can be actively operated by the subject. The user may be enabled to choose between certain preconditions in generating the tactile output signal, for example, to choose between a slower or faster breathing sequence at the beginning of the starting phase (P2). However, there can be still the influence of a signal pattern that has been previously recognized so that the generated sequence of tactile output signals can be still adapted to the user and is personalized to a certain extent.

Although this is not shown in the present embodiment in FIG. 1, it is possible to provide the tactile breath pacing system 10 with display devices that show the user the operation state of the tactile breath pacing system 10. Such a display device can be a visual display, a light source like a LED or an audio display device giving a sound feedback to the user. This display device can also be arranged externally so that it is not integrated into the tactile output unit 12.

Figure 4:
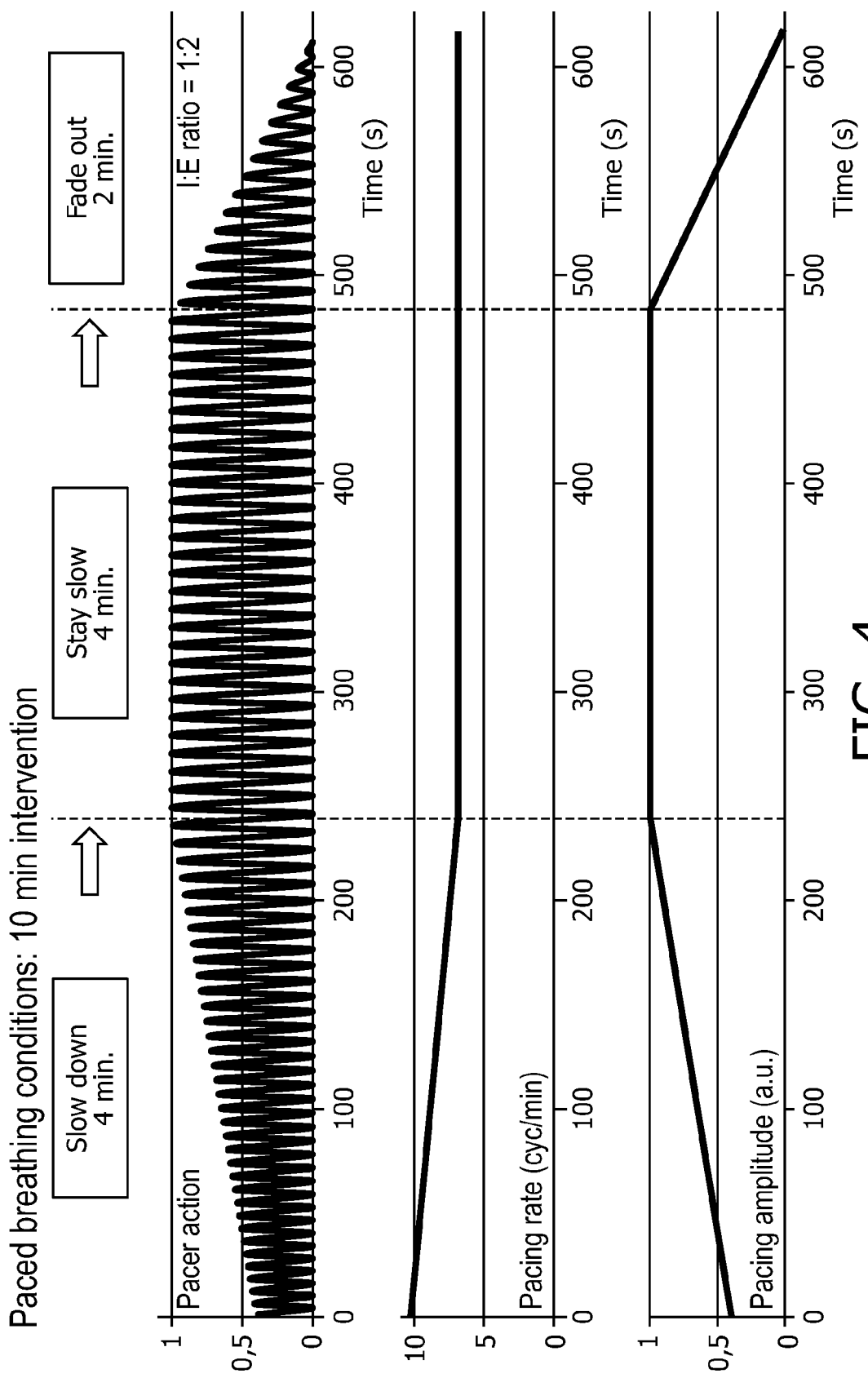

To further explain the change of the characteristics of the tactile output signal in the phases (P3), (P4) and (P5), reference is made to FIG. 4, showing the development of the pacer action over time (horizontal axis) with respect to pacing rate and amplitude. FIG. 4 shows three different curves. The upper curve shows the actual movement (pacer action) of the tactile output unit 12 over time (horizontal axis), the amplitude of this movement extending on the vertical axis. The second curve from above shows the development of the pacing rate (vertical axis) over time, while the third curve shows the development of the pacing amplitude (vertical axis). The amplitude of the pacer action in the upper and the lower curve has been normalized to a value of 1 as a maximum, while the pacing rate is given in pacing cycles per minute.

The development of the pacing rate corresponds to that in FIG. 3, i.e. it decreases in a slow down phase (P3) that lasts for 4 minutes in the present example but stays on a constant level in the following phase (P4) for another 4 minutes and the fade out phase (P5) of 2 minutes. However, the development of the pacing amplitude is different, as it is already indicated in the upper curve. The lower curve shows this development even more clearly: In phase (P3), the amplitude rises linearly towards its maximum, that is reached at the transition from phase (P3) to (P4), stays on a constant level in (P4) and decreases linearly to zero during phase (P5).

Moreover, a speaker and/or a display integrated into or connected to the tactile output unit 12 can be used to output instructions to the user on how to use the device. It is further noted that any input unit 14 as described above can also be connected by wire or wirelessly to the tactile output unit 12.

The output unit may preferably include a temperature controlling element, which could be used to warm up the output unit. Such temperature controlling element could be realized as a heating element, which is just controlled to have fixed temperature and/or which may have a temperature sensor for sensing the temperature of the user who contacts the output unit. By warming up the output unit convenience of the user in increased. Thus in case of a cushion or hand pad or the like people having colder hands or feeling cold may feel more comfortable. On the other hand it can increase feeling of connectedness with the output unit. This temperature control of the pad can be realized by integration of a heating element in the pad.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A breath pacing system for pacing a respiratory activity of a subject, comprising:
    an input unit generating an input signal related to a respiration characteristic of the subject, the respiration characteristic comprising at least one of an inhale phase and an exhale phase,
    a signal analyzing unit recognizing a signal pattern within the input signal, and
    an output unit outputting output signals corresponding to a desired breathing sequence,
    wherein said output unit, upon receiving a starting signal, outputs a sequence of output signals having a beginning and comprising a signal pattern related to a previously recognized signal pattern, and
    said sequence of output signals begins with an expand time of the output unit corresponding to the present inhale time of the subject or a contract time of the output unit corresponding to the present exhale time of the subject, said sequence of output signals transitions to a slow down phase independent of the input signal, wherein in the slow down phase, a frequency of the output signals in the sequence is decreased and an amplitude of the output signals in the sequence is increased in the slow down phase until the desired breathing sequence is reached.

2. The breath pacing system according to claim 1, wherein the output unit is provided as a tactile output unit for outputting tactile output signals.

3. The breath pacing system according to claim 1, wherein the input unit is integrated into the output unit.

4. The breath pacing system according to claim 1, wherein the input unit comprises a user interface for receiving a user input for adjusting a characteristic of the sequence of output signals.

5. The breath pacing system according to claim 4, wherein the input unit comprises at least one of a mouse wheel, a keyboard, at least one button, a touch screen, a touch pad, a squeeze sensor or a pressure switch.

6. The breath pacing system according to claim 1, wherein the input unit comprises a sensor for sensing a characteristic of the subject.

7. The breath pacing system according to claim 1, wherein the starting signal is generated upon the signal analyzing unit recognizing the signal pattern gained within at least one monitoring phase having a length for monitoring the respiratory activity of the subject.

8. The breath pacing system according to claim 7, wherein the length of the monitoring phase is controlled depending on the respiratory activity of the subject within the monitoring phase.

9. A breath pacing system according to claim 1, wherein the sequence of output signals starts with a signal pattern related to a signal pattern gained within a previous monitoring phase.

10. The breath pacing system according to claim 9, wherein the sequence of output signals starts with at least one of a frequency, an amplitude related to a frequency, an inhale to exhale ratio, or an amplitude contained in a signal pattern acquired from a previous monitoring phase.

11. The breath pacing system according to claim 1, wherein the amplitude of the output signal is increased in the slow down phase.

12. A breath pacing system according to claim 1, wherein the sequence of output signals comprises a fade out phase in which the amplitude of the output signal is decreased.

13. A method for pacing a respiratory activity of a subject, the method comprising:
    generating, using an input unit, an input signal related to a respiration characteristic of the subject, the respiration characteristic comprising at least one of an inhale phase and an exhale phase,
    recognizing, using a signal analyzing unit, a signal pattern within the input signal, and
    outputting, using an output unit, output signals corresponding to a desired breathing sequence,
    wherein said sequence of output signals comprises a signal pattern related to a previously recognized signal pattern, and
    said sequence of output signals begins with an expand time of the output unit corresponding to the present inhale time of the subject or a contract time of the output unit corresponding to the present exhale time of the subject, said sequence of output signals transitions to a slow down phase independent of the input signal, wherein in the slow down phase, a frequency of the output signals in the sequence is decreased and an amplitude of the output signals in the sequence is increased in the slow down phase until the desired breathing sequence is reached.

14. The method of claim 13, wherein the output unit is provided as a tactile output unit for outputting tactile output signals.

15. The method of claim 13, wherein the input unit is integrated into the output unit.

16. An output unit for pacing a respiratory activity of a subject, comprising:
an input unit generating an input signal related to a respiration characteristic of the subject, the respiration characteristic comprising at least one of an inhale phase and an exhale phase,
a signal analyzing unit recognizing a signal pattern within the input signal, and an actuator that induces movement of the output unit to output signals corresponding to a desired breathing sequence, said actuator, upon receiving a starting signal, moves, which causes the output unit to output a sequence of output signals having a beginning and comprising a signal pattern related to a previously recognized signal pattern, and said sequence of output signals transitioning to a slow down phase that is independent of the input signal in which a frequency of the output signals in the sequence is decreased and an amplitude of the output signals in the sequence is increased in the slow down phase, wherein said sequence of output signals begins with an expand time of the output unit corresponding to the present inhale time of the subject or a contract time of the output unit corresponding to the present exhale time of the subject.

17. The output unit of claim 16 further comprising a user interface that presents status information about the output unit.

18. The output unit of claim 16, wherein based on receipt of the sequence of output signals, the output unit changes shape.

19. The output unit of claim 16, wherein based on receipt of the sequence of output signals, the output unit changes size.

* * * * *